(12) United States Patent
Matera, Jr.

(10) Patent No.: US 6,685,719 B2
(45) Date of Patent: Feb. 3, 2004

(54) SURGICAL TATTOOING APPARATUS AND METHOD

(76) Inventor: James R. Matera, Jr., 223 Cambon Ave., St. James, NY (US) 11780

( * ) Notice: Subject to any disclaimer, the term of this patent is extended or adjusted under 35 U.S.C. 154(b) by 100 days.

(21) Appl. No.: 09/809,521

(22) Filed: Mar. 15, 2001

(65) Prior Publication Data

US 2001/0037124 A1 Nov. 1, 2001

Related U.S. Application Data

(60) Provisional application No. 60/189,392, filed on Mar. 15, 2000.

(51) Int. Cl.$^7$ .............................................. A61B 17/34
(52) U.S. Cl. ..................................................... 606/186
(58) Field of Search ................................ 606/186, 185, 606/116, 223, 187, 188, 189; 81/9.22, 438; 604/272, 181, 187; 128/303 R, 316, 355, 329; 401/5, 105, 115

(56) References Cited

U.S. PATENT DOCUMENTS

| | | | | |
|---|---|---|---|---|
| 4,665,912 A | * | 5/1987 | Burton | 128/303 R |
| 4,671,277 A | * | 6/1987 | Beuchat | 128/316 |
| 5,472,449 A | * | 12/1995 | Chou | 606/186 |
| 6,030,404 A | * | 2/2000 | Lawson et al. | 606/186 |
| 6,197,034 B1 | * | 3/2001 | Gvozdic et al. | 606/116 |
| 6,345,553 B1 | * | 2/2002 | Adler et al. | 81/9.22 |

* cited by examiner

Primary Examiner—A. Vanatta
Assistant Examiner—Alissa L. Hoey
(74) Attorney, Agent, or Firm—Carter DeLuca Farrell & Schmidt LLP (57) ABSTRACT

Instrumentation and a method for facilitating surgical tattooing in connection with radiation thereby incorporating a novel ink dispensing instrument having sterile tattoo ink. The dispensing instrument is connectable to a surgical tattoo needle to ensure the delivery of sterile ink during each procedure. Subsequent to demarcation, the instrument and needle may be discarded.

15 Claims, 8 Drawing Sheets

SURGICAL TATTOOING APPARATUS AND METHOD

This application claims the benefit of U.S. Provisional Application No. 60/189,392 filed on Mar. 15, 2000.

BACKGROUND OF THE INVENTION

The present invention relates to a surgical apparatus and method for tattooing a patient for a surgical procedure, and, more particularly to a universal procedure and associated instrumentation for tattooing radiation patients for purposes of identifying target points for repetitive radiation.

Tattooing in a hospital setting must be sterile. Any injection received in a hospital setting should be as clean as possible to reduce patient harm. Current methods for patient demarcation or tattooing in conjunction with radiation therapy utilize unsterile modalities for applying the ink for the tattoo. In a typical procedure, the ink is provided in a common inkwell which is subject to a number of contaminants during use. Specifically, the inkwell becomes contaminated once it is opened. Thereafter, the repetitive insertion of tattooing needles/syringes on multiple patients introduces additional contaminants which, may additionally increase the potential for transmission of infectious diseases between subsequent patients.

SUMMARY OF THE INVENTION

Accordingly, the present invention is directed to a new standard procedure or protocol, and associated instrumentation, for applying a surgical tattoo. In a preferred embodiment, a method for surgically tattooing a patient, comprises the steps of providing a sealed ink dispensing instrument having sterilized tattoo ink therein and defining a port for dispensing said tattoo ink, dispensing the tattoo ink from the port of the ink cartridge, directing the tattoo ink with respect to predetermined body tissue of a patient to mark the body tissue and disposing the ink cartridge after use on the patient. The ink dispensing instrument may have a deformable ink cartridge with the tattoo ink therein whereby the step of dispensing includes deforming the ink cartridge to dispense the tattoo ink under pressure. A needle may be connected to the ink cartridge adjacent the port such that the tattoo ink is passed through a lumen in the needle to mark the predetermined body tissue.

A surgical ink dispensing instrument for facilitating surgical tattooing of a patient is also disclosed. The dispensing instrument includes an ink cartridge defining an internal chamber, and having a port in communication with the internal chamber and sterile tattoo ink disposed within the internal chamber of the ink cartridge. The ink cartridge may be substantially flexible to permit the operator to deform the ink cartridge to expel the tattoo ink through the port. An end cap is removably mounted to the ink cartridge about the port to substantially enclose the port. The ink cartridge may define a generally elongated portion for engagement by the user.

The method and instrumentation of the present invention ensures the use of sterile tattoo ink in each tattooing procedure thereby overcoming disadvantages of current practices used for surgical tattooing.

BRIEF DESCRIPTION OF THE PREFERRED EMBODIMENTS

Preferred embodiments of the present invention will be better understood with reference to the drawings wherein.

DETAILED DESCRIPTION OF THE PREFERRED EMBODIMENTS

The preferred embodiment of the method and instrumentation disclosed herein are discussed in conjunction with a surgical tattooing procedure for radiation therapy. It is envisioned, however, that the invention may be applicable to a variety of procedures including, non-surgical tattooing procedures.

The following discussion includes a description of the instrumentation utilized in applying a surgical tattoo followed by a description of the preferred method or protocol utilizing the instrumentation Referring now to the drawings wherein like reference numerals identify similar like elements throughout the several views, FIGS. 1–4 illustrate a preferred ink dispensing instrument in accordance with the present invention. Tattoo ink dispensing instrument 10 includes essentially three elements, namely, ink cartridge 12, leading cap 14 and trailing cap 16. Ink cartridge 12 defines internal cavity 18 which accommodates the sterile ink. Ink cartridge 12 has a generally frustoconical outer shape or configuration with an enlarged trailing end 20 which gradually tapers to a smaller leading end 22. Leading end 22 defines a narrowed distribution port 24 which has an internal lumen 26 communicating with the internal cavity 18 of ink cartridge 12.

Trailing end 20 of ink cartridge 12 includes a circumferential collar 28 to which trailing cap 16 is mounted. In the preferred embodiment, trailing cap 16 includes a transverse outer wall 30 which is joined to circumferential collar 28 of ink cartridge by conventional means, including for example adhesives, cements, snap fit threaded means. In the preferred embodiment, trailing cap 16 is joined to the ink cartridge 12 through an ultrasonic welding technique. Trailing cap 16 preferably defines internal circumferential stop 32 which is received within the trailing end 20 of the ink cartridge in sealing engagement therewith.

Trailing end cap 16 defines an elongated length which facilitates functioning of the trailing end cap 16 as a handle. Preferably, in use the operator holds end cap 16 in a manner similar to that of a writing implement thus providing ease of control and a degree of familiarity to the operator.

Leading cap 14 is placed on ink cartridge 12 prior to loading of the ink and preferably includes an internal stop 34 which is received within the lumen 26 of the port 24 to fluidly seal the port 24 at this end. Leading cap 14 further defines an internal circumferential wall 36 which is mounted about the port 24 and preferably dimensioned so as to frictionally engage the port 24 to thereby retain the end cap 14 on the ink cartridge during assembly and shipping.

Figure 4:
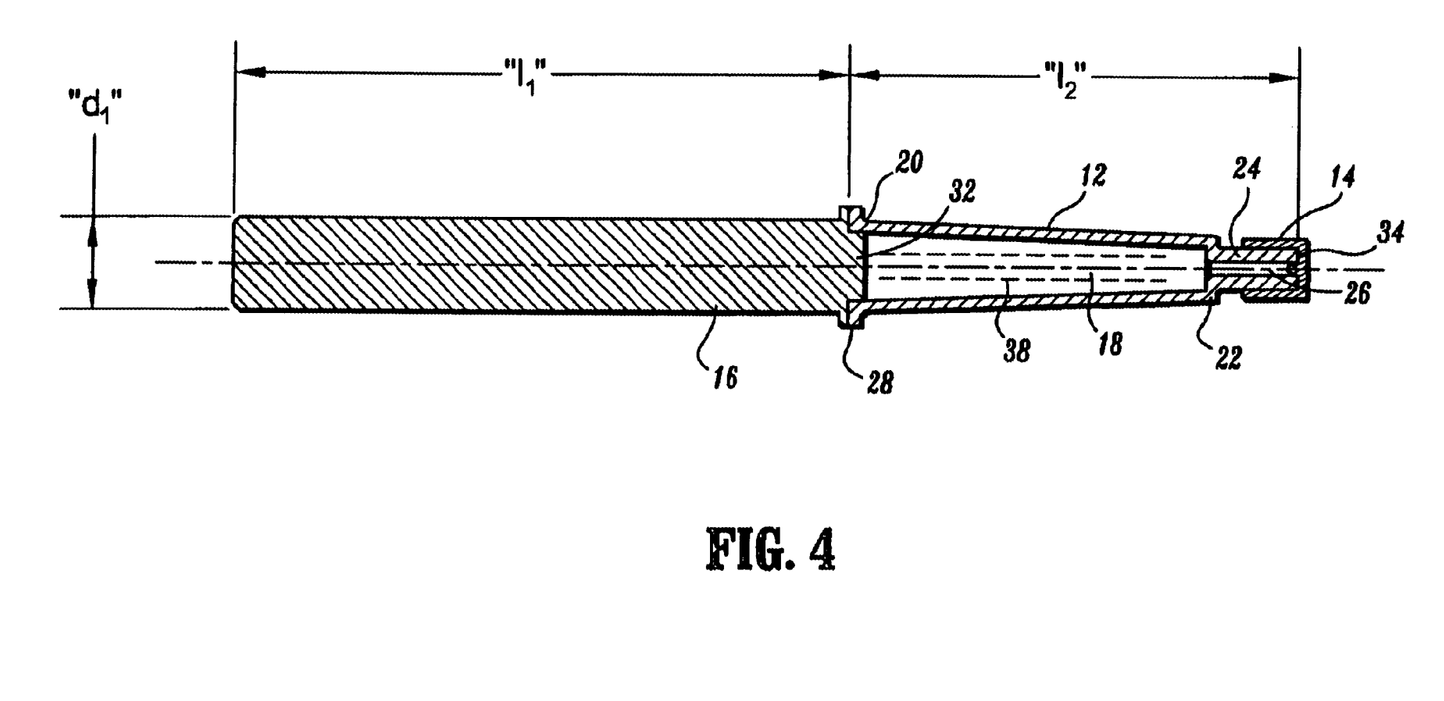
FIG. 4 is a cross-sectional view of the dispensing instrument.

As best depicted in FIG. 4, the tattoo ink 38 (represented as - -) filled within ink cartridge 12 is and is FD&C approved sterile tattoo ink which is the only ink permitted for human skin tattooing. Various colors are contemplated.

The components of the instrument 10 are preferably fabricated from a suitable polymeric material by known injection molding techniques. Ink cartridge 12 may have some rigidity to minimize deformation thereof whereby the tattoo ink is gravity fed through distribution port 24. Alternatively, ink cartridge 12 may be flexible to be squeezed in a manner to force the tattoo ink through distribution port 24. Trailing end cap 16 is preferably rigid.

The preferred dimensions of the instrument are as follows:

$l_1$—length of trailing end cap: 2–3 inches, preferably about 2.5 inches $l_2$—length of cartridge: 1.5–2.1 inches, preferably about 1.8 inches $d_1$—diameter of trailing end cap: 0.250–0.450 inches, preferably about 0.350 inches.

In a preferred method of manufacture, leading cap 14 is mounted to ink cartridge 12 and the ink cartridge 12 is filled with sterile FD&C approved tattoo ink. Thereafter, trailing cap 16 is then mounted to ink cartridge 12 and sealed through the ultrasonic well joint. Thus the entire device is hermetically sealed, sterile and filled with the appropriate FD&C approved tattoo ink. This device can be prepackaged and shipped and delivered to the end user.

Figure 3:
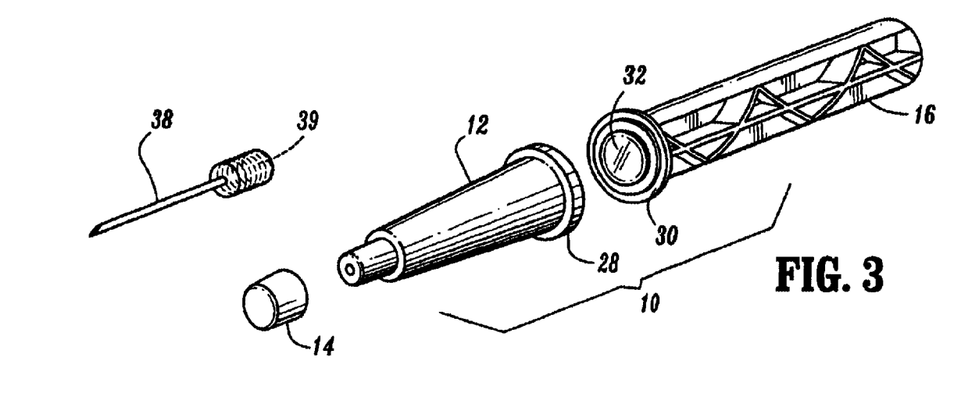
FIG. 3 is a perspective view with parts separate of the dispensing instrument of FIG. 1.

The ink dispensing instruments of the afore-described embodiments are intended for use in conjunction with a tattoo needle 38 depicted in FIG. 3 which may be secured to the device through any number of known conventional means. For example, the needle 38 can be mounted about the distal port and connected therewith with threaded means (shown in phantom) on the needle 38 as internal threads 39 which threadably engage corresponding threads (not shown) of cartridge 12, a bayonet coupling, a frictional engagement, etc. Alternatively, the needle is not required and the ink from the ink cartridge can be dispensed onto a needle point which is subsequently applied to the skin of the patient for tattooing.

Figures 1, 2:
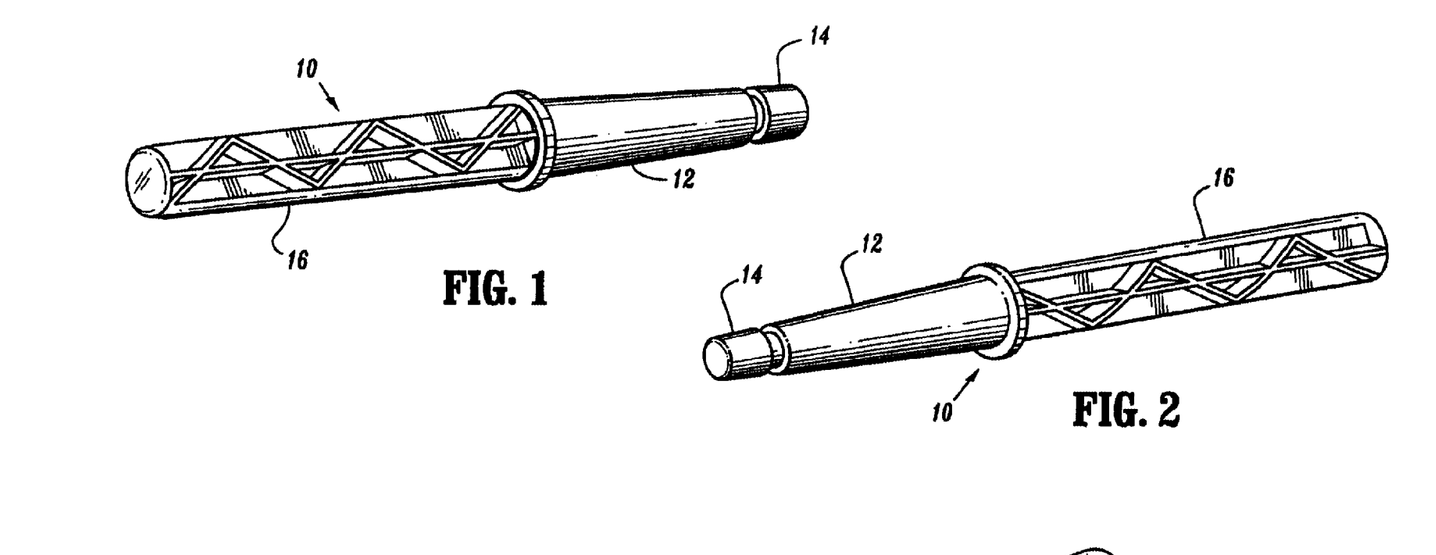
FIGS. 1–2 are frontal and rear perspective views of an ink dispensing instrument for use in accordance with the principals of the present invention.
Figures 5, 6:
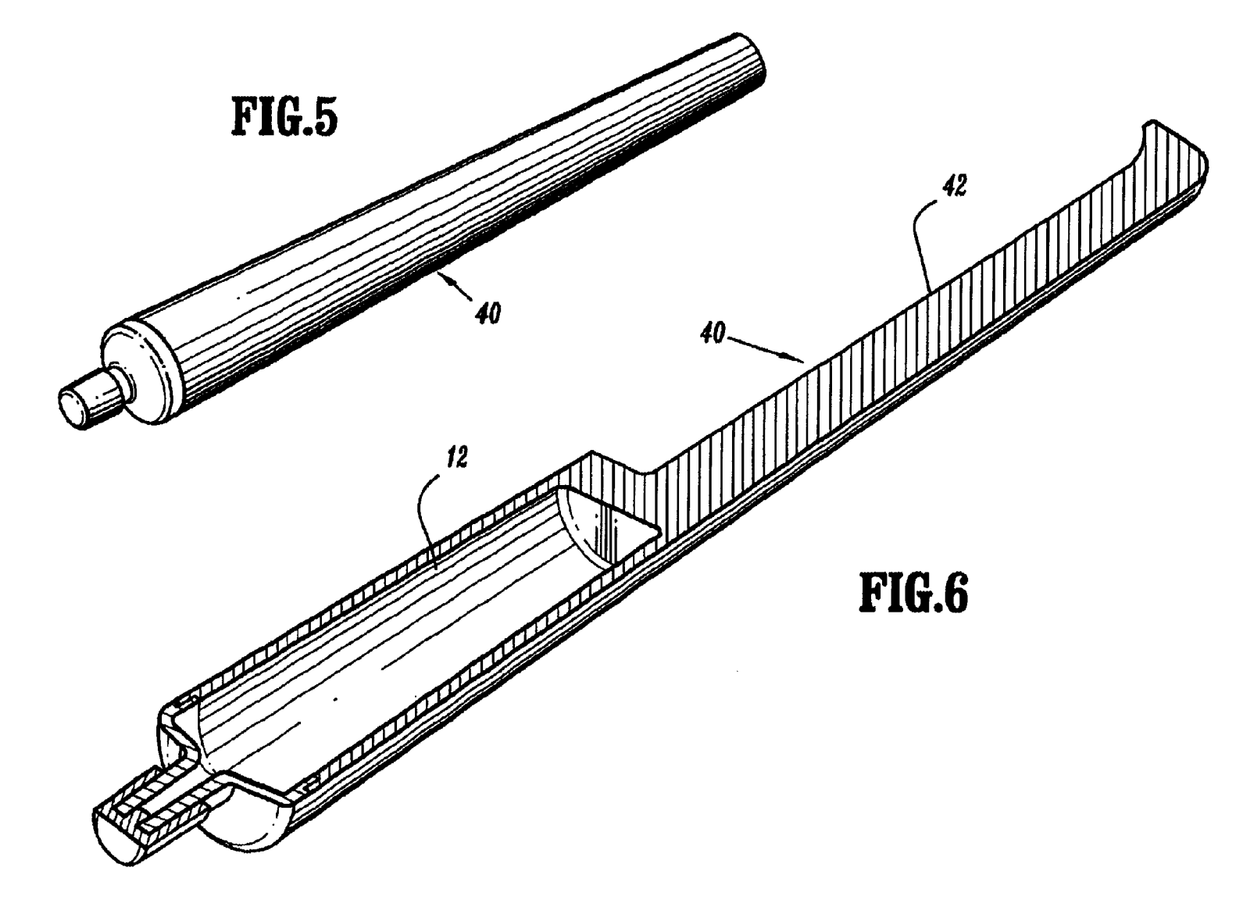
FIG. 5 is a perspective view of an alternate embodiment of the ink dispensing instrument of FIG. 1.
FIG. 6 is a cross-sectional view of the dispensing instrument of FIG. 5.
Figure 7:
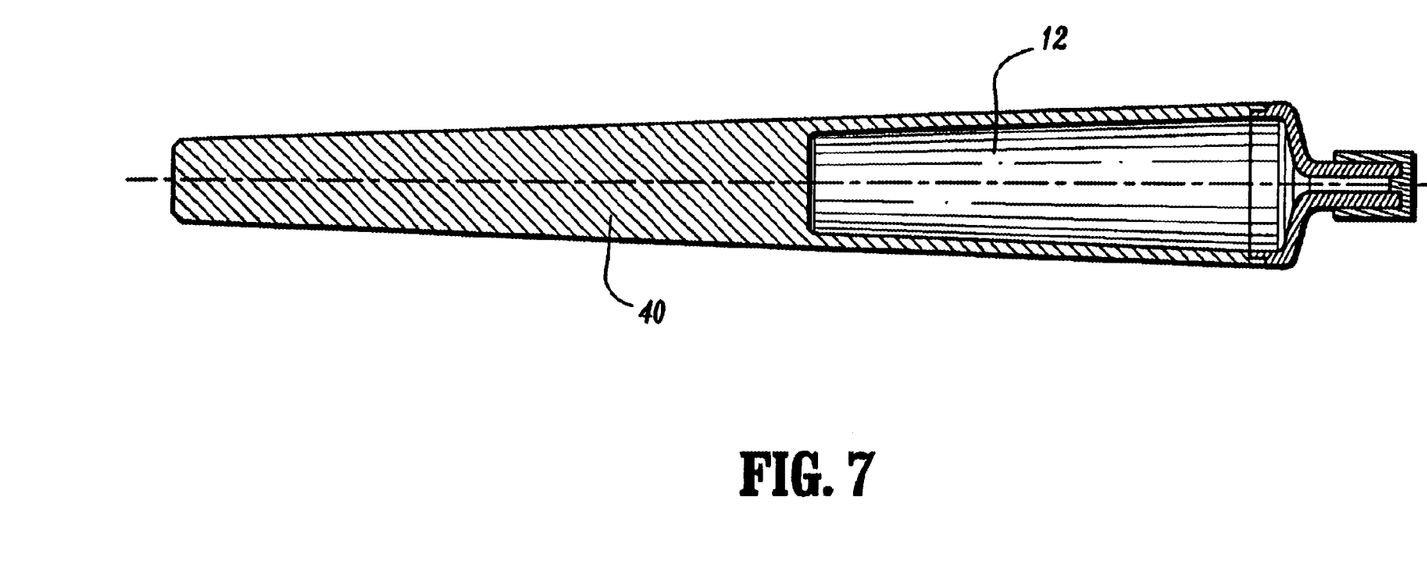
FIG. 7 is a side cross-sectional view of the dispensing instrument.
Figures 8, 9:
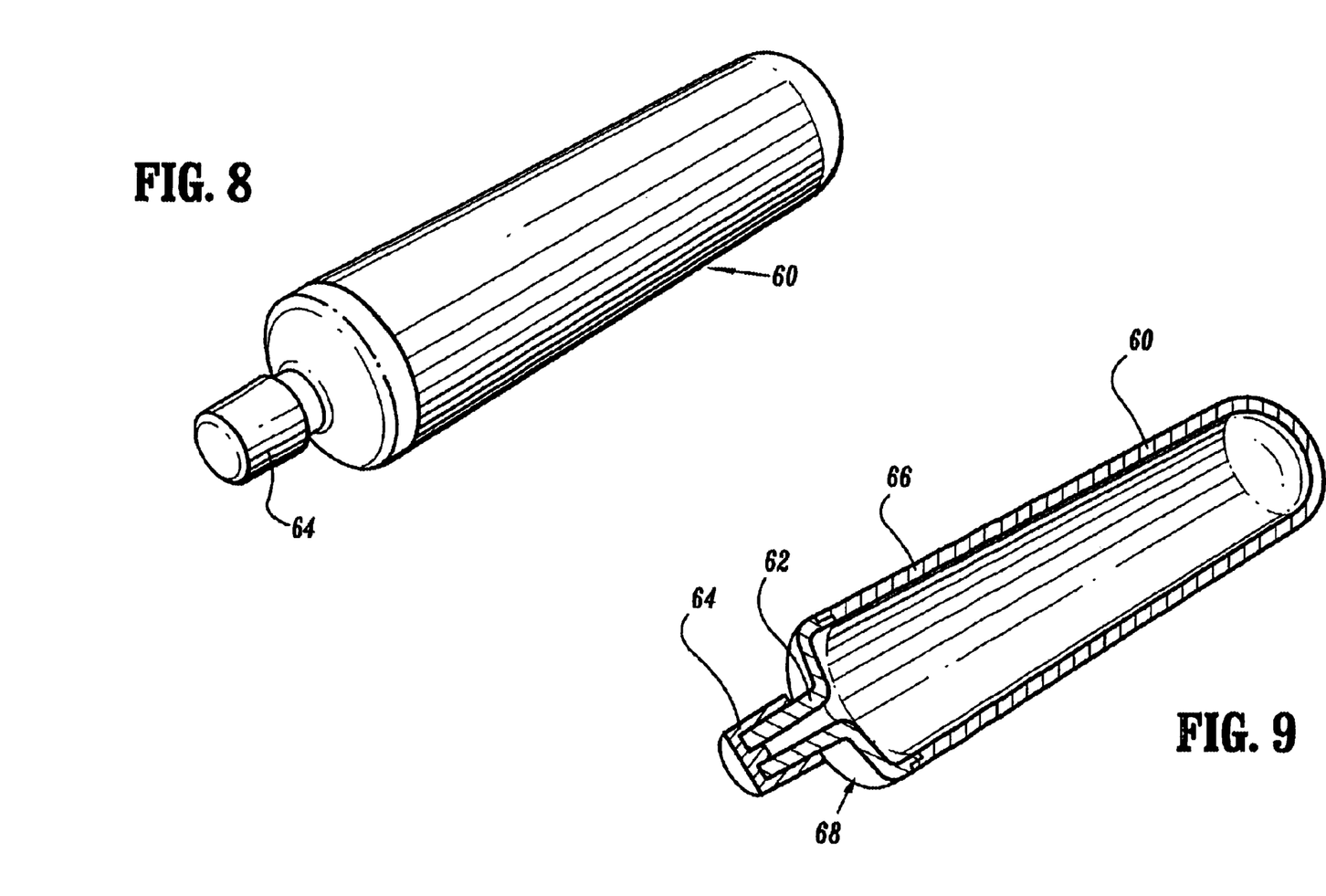
FIG. 8 is a perspective view of another alternate embodiment of the ink dispensing instrument of FIG. 1.
FIG. 9 is a cross-sectional view of the dispensing instrument of FIG. 8.
Figure 10:
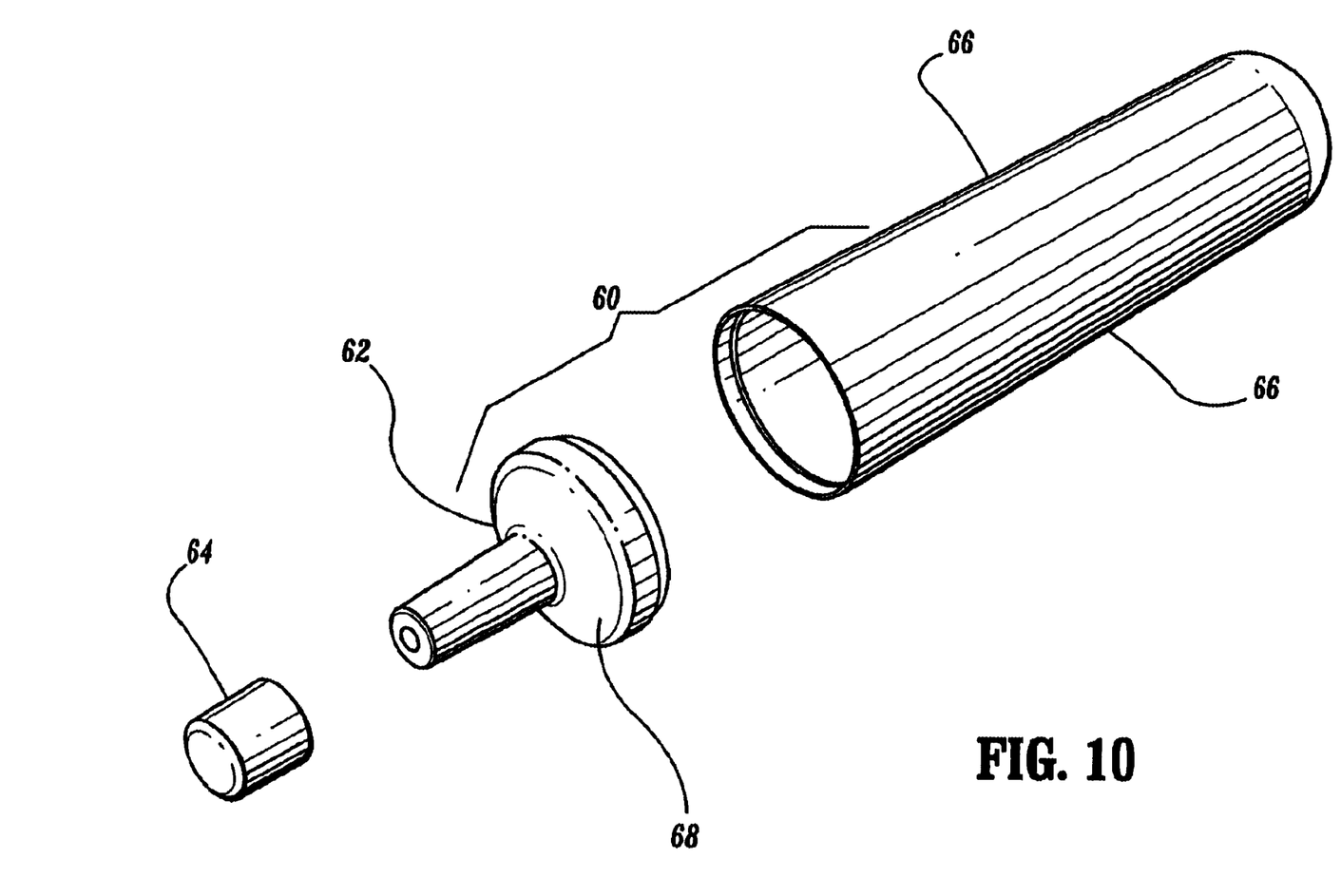
FIG. 10 is a perspective view with parts separated of the dispensing instrument.
Figure 11:
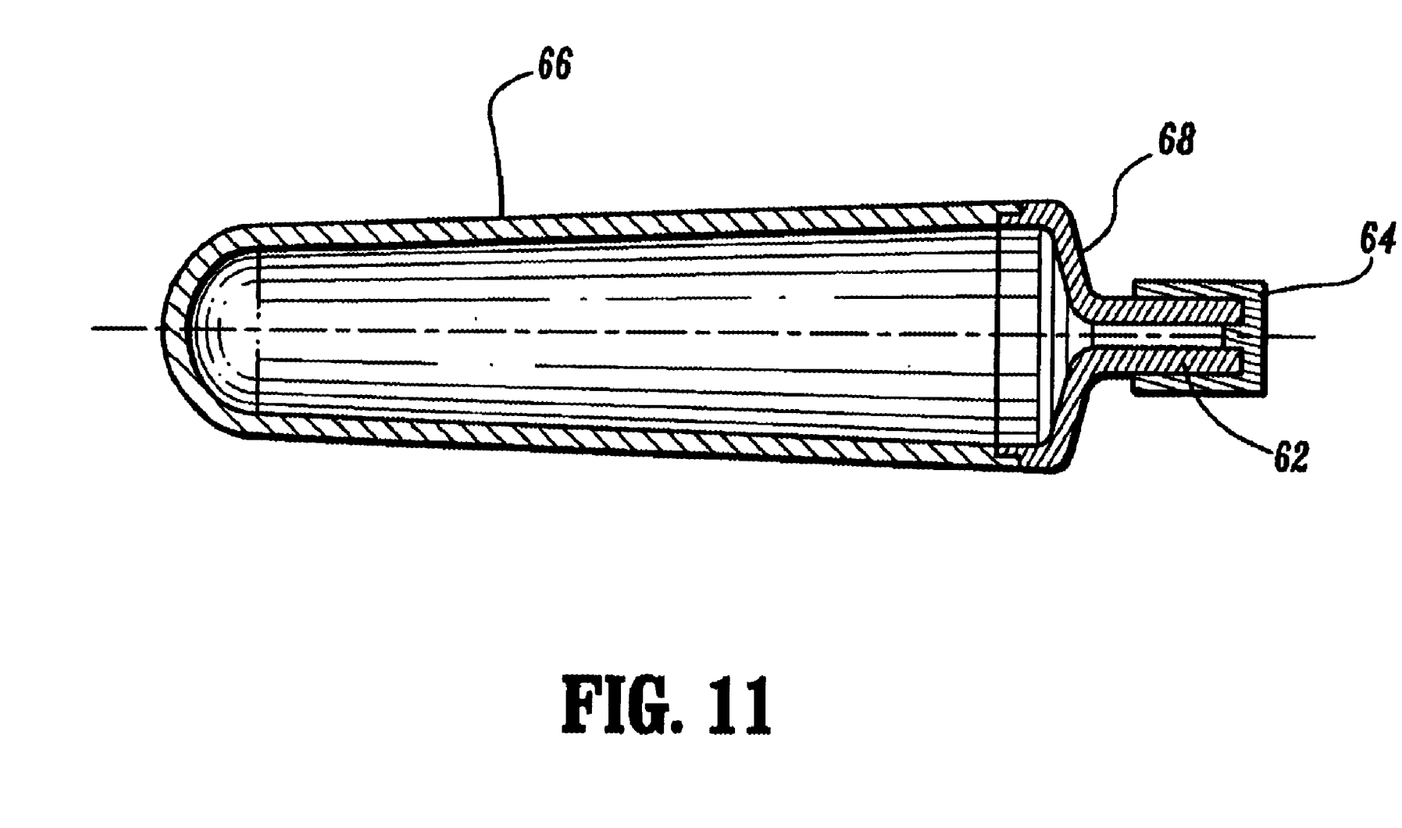
FIG. 11 is a side cross-sectional view of the dispensing instrument.

FIGS. 5–7 illustrate an alternate embodiment of the dispensing instrument of FIG. 1. In this embodiment, the trailing cap is eliminated. Ink cartridge 12 has an elongated portion or handle 40 adjacent its trailing end and integrally forward therewith during injection molding. The handle includes recessed grooves 42 (best depicted in FIG. 6) which accommodate the fingers of the user. The elongated portion on handle 40 enables the operator to hold the instrument in a manner similar to using a pencil or pen. This provides the user with a familiar feel that enhances control when applying the tattoo. This instrument defines a length ranging from 4.00–4.50 inches, preferably about 4.25 inches.

FIGS. 8–11 illustrate another embodiment of the present invention. The device in these figures is substantially similar to the prior embodiment and includes an ink cartridge 60 defining a generally bulbous shape which is rounded at its proximal end. The distal end of the ink cartridge 60 includes a distal port 62 and has an end cap 64 which is mounted to the distal port in the manner discussed above. The ink cartridge 60 may comprise two components, namely, the ink base cartridge 66 and a nozzle 68 which defines the distal port 62 and is ultrasonically welded to the base 66 to connect the two components. The bulbous ink cartridge 60 facilitates holding of the instrument between the index and middle finger, and the thumb and provides a greater area to facilitate squeezing or deformation of the ink cartridge to expel the sterile tattoo ink.

Surgical Tattooing Protocol

Figure 12:
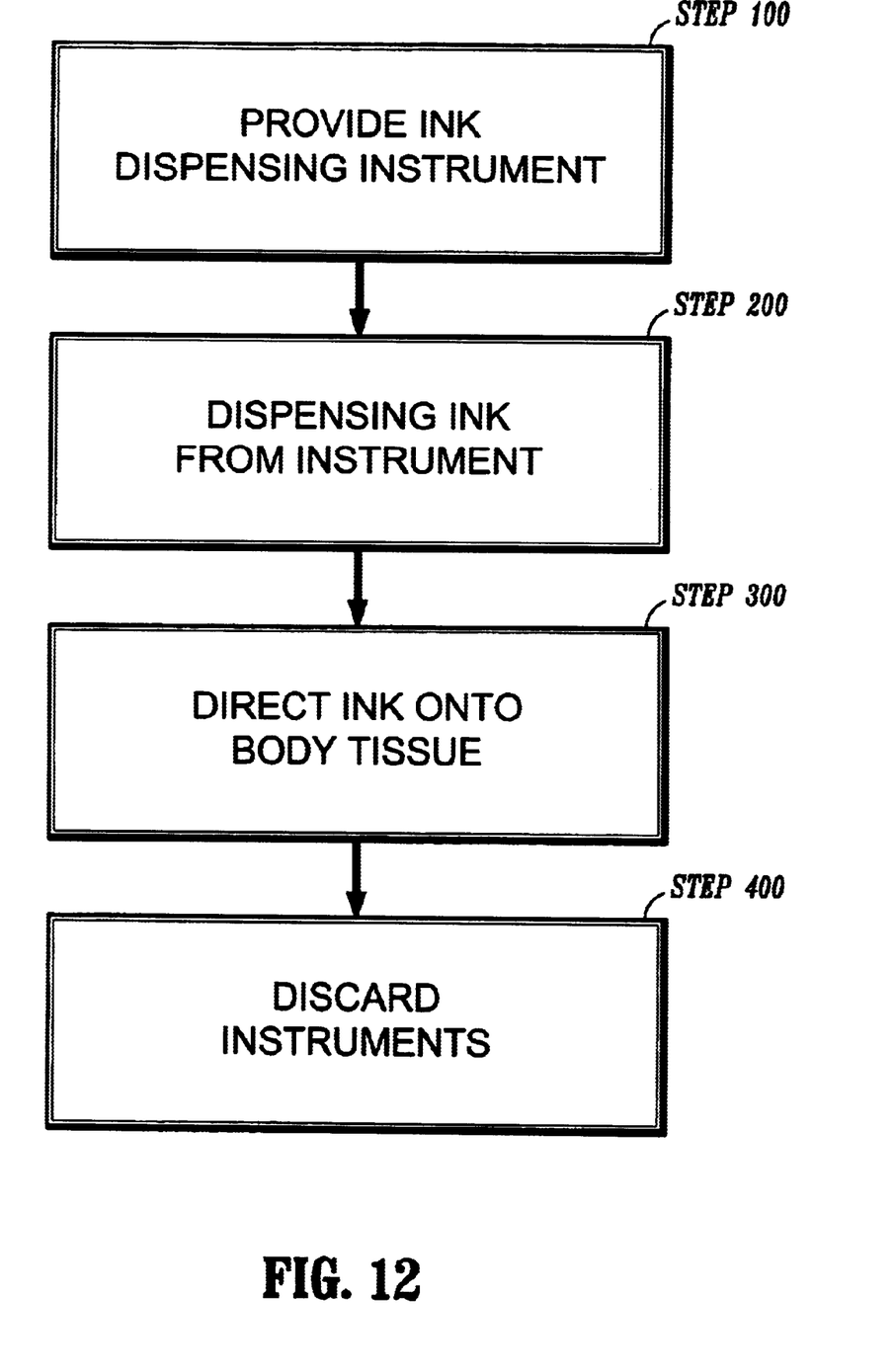
FIG. 12 is a flow chart illustrating the preferred procedure for applying a surgical tattoo with the instrumentation.

The preferred surgical tattooing protocol with the instrumentation will now be discussed with reference to the flow chart of FIG. 12. In step 100, the prepackaged ink dispensing instrument is provided and opened by tattooing personnel. A sterilized tattooing needle 38 is mounted to ink cartridge 16 as discussed hereinabove. Alternatively, if desired, a mounted tattooing needle is not utilized. The needle is then introduced to the skin of the patient. With reference to steps 200, 300, the ink cartridge is dispensed (step 200) or squeezed (or if gravity fed no squeezing is required) to deliver the ink through distal port into the needle and then directed (step 300) into the skin of the patient. After use, the needle and ink cartridge are discarded (step 400). In an alternate arrangement, a tattooing needle is not mounted to the ink cartridge, but, is introduced within the skin. Thereafter, the tattoo ink is applied to the outer surface of the needle to travel along the needle into the tissue.

It is contemplated that the dispensing instrument of the present invention will be individually wrapped in a sterile packet attached and boxed. The packets will be attached to each other and an operator would pull off one packet at a time when needed. See, e.g., the dispensing system disclosed in U.S. Pat. Nos. 5,358,140 and 5,282,349, the contents of each being incorporated herein by reference. The novel instruments will be used for safe and sterile application of permanent tattoo dots on skin for purposes of identifying points of interest. The predominant use would be on radiation patients although other uses are envisioned as well.

The present apparatus will lower medical wastes in department. In accordance with the present invention, the instrument is preloaded with permanent or semi-permanent ink dye. The preloaded instrument would be used to penetrate the skin at predetermined locations and thereafter activated to deliver the ink dye to appropriately tattoo the patient for, e.g., successive radiation treatments. After use, the instrument would be disposed although it is envisioned that the syringe could be sterilized for subsequent use(s).

The present invention thus contemplates the aforediscussed surgical tattooing apparatus and a method for tattooing a patient utilizing the apparatus. The system assures that sterile tattoo ink is used for each individual patient.

While the above description contains many specifics, these specifics should not be construed as limitations on the scope of the disclosure, but merely as exemplifications of preferred embodiments thereof. Those skilled in the art will envision many other possible variations that are within the scope and spirit of the invention

What is claimed is:

1. A method for surgically tattooing a patient for use in conjunction with radiation therapy, comprising the steps of:
   providing a sealed ink dispensing instrument having sterilized tattoo ink therein and defining a port for dispensing said tattoo ink;
   dispensing said tattoo ink from said port of said dispensing instrument;
   directing said tattoo ink with respect to predetermined body tissue of a patient to mark the body tissue to generally correspond to a target location for radiation therapy; and
   disposing said dispensing instrument after use on the patient.

2. The method according to claim 1 wherein said ink dispensing instrument includes a deformable ink cartridge having said tattoo ink therein and wherein said step of dispensing includes manually deforming said ink cartridge by user engagement of said ink cartridge to dispense said tattoo ink under pressure.

3. The method according to claim 2 further including the step of connecting a needle to said ink cartridge adjacent said port and wherein said step of directing includes passing said tattoo ink through a lumen in said needle to mark the predetermined body tissue.

4. The method according to claim 3 wherein said step of directing includes penetrating the predetermined body tissue with said tattoo needle.

5. The method according to claim 2 wherein said ink cartridge includes means for mounting a needle thereto and further including the step of mounting said needle to said dispensing instrument adjacent said port.

6. The method according to claim 1 wherein said step of directing includes penetrating the predetermined body tissue with a tattoo needle and applying said tattoo ink to said tattoo needle.

7. The method according to claim 1 wherein said ink dispensing instrument includes an ink cartridge having an internal cavity for accommodating said tattoo ink.

8. The method according to claim 1 further including the step of performing at least one radiation treatment directed at the target location as identified by the mark on the body tissue.

9. The method according to claim 8 including the step of performing successive radiation treatments directed at the target location as identified by the mark on the body tissue.

10. The method according to claim 1 wherein said dispensing instrument includes means for mounting a needle thereto and further including the step of mounting said needle to said dispensing instrument adjacent said port.

11. A surgical ink dispensing instrument for facilitating surgical tattooing of a patient, which comprises:
    an ink cartridge defining an internal chamber, said ink cartridge defining a port in communication with said internal chamber and having means for releasably mounting a needle adjacent said port;
    sterile tattoo ink disposed within said ink cartridge; and
    an end cap removably mounted to said ink cartridge about said port to substantially enclose said port.

12. The surgical instrument according to claim 11 wherein said ink cartridge is substantially flexible to permit the operator to manually deform said ink cartridge by direct engagement of said ink cartridge with a hand of the operator to expel said tattoo ink through said port.

13. The surgical instrument according to claim 11 wherein said ink cartridge defines a generally elongated portion for engagement by the user.

14. The surgical instrument according to claim 11 including a surgical needle mounted to said means for releasably mounting said ink cartridge.

15. The surgical instrument according to claim 14 wherein said surgical needle defines a lumen in communication with said port of said ink cartridge.

* * * * *